United States Patent [19]
Rentsch

[11] Patent Number: 5,952,399
[45] Date of Patent: Sep. 14, 1999

[54] POLYMERISABLE DENTAL MATERIAL AND USE OF APATITE FILLERS IN THE DENTAL MATERIAL

[75] Inventor: Harald Rentsch, Hanover, Germany

[73] Assignee: Degussa Aktiengesellschaft, Frankfurt, Germany

[21] Appl. No.: 08/941,549

[22] Filed: Sep. 30, 1997

[30] Foreign Application Priority Data

Sep. 30, 1996 [DE] Germany .............. 196 40 454

[51] Int. Cl.⁶ .................. A61K 6/083; C08K 3/32
[52] U.S. Cl. .................. 523/116; 523/114; 523/115; 524/414; 524/415; 501/45; 423/306; 423/307
[58] Field of Search .................. 523/114, 115, 523/116; 524/414, 415; 423/306, 307; 501/45

[56] References Cited

U.S. PATENT DOCUMENTS

| | | | |
|---|---|---|---|
| 4,131,597 | 12/1978 | Bluethgen et al. | 623/16 |
| 4,775,646 | 10/1988 | Hench et al. | 501/1 |
| 4,778,834 | 10/1988 | Murray . | |
| 4,869,906 | 9/1989 | Dingeldein et al. | 523/116 |
| 5,304,577 | 4/1994 | Nagata . | |

FOREIGN PATENT DOCUMENTS

| | | | |
|---|---|---|---|
| 0 193 588 | 8/1985 | European Pat. Off. . | |
| 0 625 490 | 11/1994 | European Pat. Off. . | |
| 23 26 100 | 12/1974 | Germany . | |
| 25 01 683 | 1/1975 | Germany . | |
| 39 32 469 | 4/1990 | Germany . | |
| 2130187 | 5/1985 | United Kingdom | 423/306 |
| WO 94/23944 | 10/1994 | WIPO . | |

OTHER PUBLICATIONS

Antonucci et al., "Filler Systems Based on Calcium Metaphosphates", Dent Mater 7:124–129 (Apr. 1991).
Derwent Abstract No. J59216807 (1984).
Derwent Abstract No. J59217666 (1984).

*Primary Examiner*—Andrew E. C. Merriam
*Attorney, Agent, or Firm*—Pillsbury Madison & Sutro LLP

[57] ABSTRACT

A dental material based on an organic polymerisable binding agent has a content of A) one or more mixed apatites of the type
  A1) $A_{10}(XO_4)_6Z_2 + /B^*_{10-u}C^*_u(Y^*)_6Z'_2$ and/or
  A2) $A'_{10-r}(X'O_4)_{6-s}Z''_{2-t} + /B'_r(Y')_sQ_t - B''_{10-u'}C''_{u'}(Y'')_6Z'''_2$ and/or
  A3) $A''_{10-r'}(X''O_4)_{6-s'}Z'''_{2-t'} + /A'''_{r'}(X'''O_4)_{s'} + /B'''_{10-u''}C'''_{u''}(Y''')_6Z''''_2$ in which the formulae assume the significance specified in the description, in a quantity that is effective for the absorption of ions from the biological application environment of the dental material. The polymerisable dental material has variably adjustable transparency, good polishability, high strength and the capacity to release and absorb ions into and from a biological environment. Also described is a process for using the mixed apatites A1), A2) and/or A3) in polymerisable dental materials.

18 Claims, No Drawings

POLYMERISABLE DENTAL MATERIAL AND USE OF APATITE FILLERS IN THE DENTAL MATERIAL

FIELD OF THE INVENTION

The invention describes an improved polymerisable dental material having variably adjustable transparency, good polishability, high strength and the capacity to release and absorb ions into and from a biological environment. The invention is also directed towards the use of particular fillers based on apatites in the improved polymerisable dental material.

The invention relates in particular to a dental material based on polymerisable, ethylenically unsaturated monomers by way of binding agent, a catalyst for cold polymerisation, hot polymerisation and/or various types of photopolymerisation and, relative to the total weight of the dental material, 1–95 per cent by weight of an inorganic filler comprising at least one particular apatite filler.

Synthetic orthophosphates, in particular apatites such as $Ca_{10}(PO_4)_6(OH)_2$ or $Ca_{10}(PO_4)_6F_2$, are, by reason of their chemical and structural resemblance to biological hard tissues, of particular interest as materials for medical use, both on their own and in combination with other materials such as polymers, glasses, etc.

BACKGROUND OF THE INVENTION

With reference to the state of the art, the following printed publications are cited:
(1) U.S. Pat. No. 4,778,834
(2) WO-A 94/23944
(3) Antonucci, J. M., Dent. Mat. 7: 124–129, 1991
(4) EP 0 193 588 B1
(5) EP 0 625 490 A1
(6) DE 39 32 469 C2
(7) DE 23 26 100 B2
(8) DE 25 01 683 A1
(9) U.S. Pat. No. 5,304,577
(10) Derwent Abstract No. 85-021799 [04]
(11) Derwent Abstract No. 85-022140 [04].

Publication (1) describes dental materials that are produced by the combination of hydroxylapatite, $Ca_{10}(PO_4)_6(OH)_2$, in concentrations of up to 70% with polymerisable monomers. Prior to being mixed in, the hydroxylapatite particles are coated with a silicate covering and are silanised in the conventional manner for dental materials. Disadvantageous aspects of these materials are that the ion exchange (calcium, phosphate) with the environment is extensively restricted by the silicate covering and that no transparency such as is required of dental filling materials can be achieved in the material, since at 1.625 the refractive index of hydroxylapatite, $Ca_{10}(PO_4)_6(OH)_2$, is too high in comparison with the polymeric components. This results in opaque materials having only low transmission of light, as a result of which the photopolymerisation of these materials is possible only in very thin layers. Furthermore, the material is not capable of releasing fluoride ions, which are desirable in particular for dental materials, since they can act to prevent caries.

Publication (2) describes dental materials that are produced by the combinations of sintered fluorapatite, $Ca_{10}(PO_4)_6F_2$, in concentrations between 10 and 70 per cent by volume with polymerisable monomers. Although these dental materials are able to release the desired fluoride ions into their environment, they are unable to satisfy the present-day requirements as regards the translucence of dental materials, since at 1.63 the refractive index of fluorapatite, $Ca_{10}(PO_4)_6F_2$, is too high in comparison with the polymeric components employed. This likewise results in opaque materials having only low transmission of light.

With a view to overcoming this deficiency, publication (3) proposes the use of calcium metaphosphates, $[Ca(PO_3)_2]_n$, as a result of which a reduction in the refractive index to 1.54–1.59 can be achieved. Although dental materials having the desired transparency can be produced with these fillers, in comparison with fluorapatite this filler possesses a higher solubility and does not have the capacity to emit fluoride.

Therefore, with a view to the production of dental filling materials having the requisite transparency, fillers are desirable which exhibit the low solubility and the emission of fluoride as exhibited by fluorapatite but which have a refractive index lying within the range of that of the calcium metaphosphates.

In publication (4), means that contain carbon apatite and the use of carbon apatite for implants are described. However, the phosphate/carbonate apatites disclosed lack a toothlike transparency and also a strength such as is required for the region subject to masticatory pressure in the case of tooth fillings. By reason of its high opacity, the material does not cure under the action of light but is self-curing and consequently can only be used for the implant field.

Although phosphate apatites containing carbonate that are obtainable in accordance with the process of publication (5) have greater porosity and translucence, the refractive index is still inadequate. In combination with acrylates, an opaque material would result.

Antimicrobial hydroxylapatite powders are known from publication (6).

Publication (7) describes, as does publication (8), bioactive composite materials for prosthetic purposes, in particular two-phase glasses with a crystalline apatite phase embedded in a glass phase. However, with the conventional acrylate resins such materials inevitably result in cloudiness. In particular, phosphate apatites with low proportions of carbonate are described which, as is generally known, do not exhibit the required optical properties. Since the disclosed glass phase is also not opaque to X-rays, no tooth-filling materials are to be expected from the described glass-phase/apatite/acrylate combinations.

Publication (9) relates exclusively to phosphate apatites. Strontium phosphate apatite has, as does calcium phosphate apatite, a refractive index of 1.63. The problem of lowering the refractive index cannot be solved by exchanging calcium for strontium. The authors therefore aim for application in the non-visible region (cements for bone defects, tooth root, periodontium). All in all, under the conditions described, only dental materials having high opacity and insufficient strength for fillings in the visible region which is subject to masticatory pressure are obtained.

Publications (10) and (11) describe pure phosphate apatites. In combination with the named dimethacrylates, opaque pastes result. Their opacity is also discernible in that they cannot be cured with light pertaining to the visible spectrum (too little depth of penetration of the light), but rather the initiator system (amine/peroxide) has to be distributed in a two-paste material that can only be activated by mixing. Since apatite is used exclusively by way of filler, the strength of the resulting materials is too low. The stated cation substitutions and also the substitutions for X result in no reduction in the refractive index.

SUMMARY OF THE INVENTION

In view of the state of the art as specified and discussed herein it was accordingly an object of the invention to specify an improved dental material which satisfies all the demands made of a modern dental material with regard to transparency, polishability, compressive strength, absorption of water, abrasion resistance, bending strength, X-ray opacity, etc, which can be produced easily and which can be easily adapted to particular special requirements. Also an object of the invention is the specification of uses for particular apatites.

The solution that achieves these objects, is possible by means of a dental material. in which the filler component of the dental material comprises A) one or more mixed apatites of the type
  A1) $A_{10}(XO_4)_6Z_2 + /B^*_{10-u}C^*_u(Y^*)_6Z'_2$ and/or
  A2) $A'_{10-r}(X'O_4)_{6-s}Z''_{2-t} + /B'_r(Y')_sQ_t + /B''_{10-u'}C'_{u'}(Y'')_6Z''_2$ and/or
  A3) $A''_{10-r'}(X''O_4)_{6-s'}Z'''_{2-t'} + /A'''_{r'}(X'''O_4)_{s'} + /B'''_{10-u''}C''_{u''}(Y''')_6Z''''_2$ in which
  A, A', A", A'", B*, B', B" and B'" are the same or different and stand for a bivalent cation and/or a charge-equivalent combination of monovalent and trivalent cations, whereby the cations have ionic radii within the range 0.069–0.174 nm,
  X, X', X" and X'" independently of one another are the same or different and stand for a cation of valency three, four, five and/or six, whereby the cations have ionic radii within the range 0.026–0.056 nm,
  Y, Y', Y" and Y'" independently of one another are the same or different and signify $(SO_4)^{2-}$ and/or $(PO_3F)^{2-}$, optionally together with $(CO_3)^{-2}$, whereby the proportion of $(CO_3)^{2-}$ is restricted to at most ⅙, relative to the molar quantities of Y*, Y', Y" and Y'",
  Q, Z, Z', Z", Z'", Z"" and Z""' independently of one another are the same or different and stand for $F^-$, $Cl^-$, $OH^-$ or $O^{2-}$, and
  C*, C' and C" independently of one another are the same or different and are a monovalent cation, and also
  u, u' and u" independently of one another are the same or different and are an integer or fraction within the range from 0 to 6 and specify the degree of substitution of B* by C*, of B" by C' and of B'" by C" in the respective cation sublattice,
  r is an integer or fraction within the range from 0 to 10 and specifies the degree of substitution of A' by B' in the cation sublattice, r' is an integer or fraction between 0 and 9 and specifies the degree of substitution of A" by A'",
  s and s' independently of one another are the same or different and are an integer or fraction within the range from 0 to 6 and specify the degree of substitution of $X'O_4$ by Y' and of $X''O_4$ by $X'''O_4$ in the respective sublattice of the tetrahedral anions, and
  t and t' independently of one another are the same or different and are an integer or fraction within the range from 0 to 2 and specify, respectively, the degree of substitution of Z" by Q and unoccupied lattice positions for type A3), in a quantity that is effective for the absorption of ions from the biological application environment of the dental material, it is possible to create a polymerisable dental material having variably adjustable transparency, good polishability and high strength, with which it was possible, inter alia:
  a) to maintain the requisite transparency;
  b) to ensure, by means of a sufficiently low solubility of the fillers A), the bioactivity by emission of fluoride, as in the case of a fluorapatite; and
  c) to keep the refractive index of filler A) within the range of the calcium metaphosphates.

DETAILED DESCRIPTION OF THE INVENTION

Surprisingly it has been possible to show that as a result of the combination of certain apatites in the form of mixed crystals a filler can be produced which, in combination with the monomers that are customary for dental materials and optionally with other fillers such as glasses and aerosils, makes the desired transparency adjustable without having to forego the low solubility of the fluorapatites or the capacity for emission of fluoride. The refractive index of the mixed apatites is furthermore variably adjustable within certain limits, as a result of which a precise adaptation to the optical properties of the monomer combination employed is possible.

In particular, the invention encompasses dental materials having such mixed apatites for which a lowering of the refractive index of the mixed apatite is achieved as a result of the formation of the mixed apatite. This lowering of the refractive index is an important prerequisite for the optical properties of the overall filling material to be able to satisfy present-day aesthetic demands. Only by this means is the optical fit possible to the dental enamel in conjunction with the resin matrix and the other fillers that are responsible for the strength of the dental filling material.

The solutions that are known in the state of the art do not provide this benefit, since they consider mixed apatites only on the basis of phosphate apatite. Phosphate apatites have refractive indices $\geq 1.63$. For the dental filling materials that are described in accordance with the invention, however, values<1.58 are indispensable. However, these necessary changes in the optical properties can only be achieved if distinct substitutions are made in the sublattice of the complex anions—that is to say, of the phosphate anions. Within the scope of the invention this is effected by means of sulphate anions or monofluorophosphate anions, optionally combined with up to ⅙ $(CO_3)^{2-}$, relative to the total molar quantities of Y*, Y', Y" and Y'".

Consequently, the modification to the optical properties with a view to suitability for application in the visible region is not the objective in any of the patents cited at the outset, and only materials for application in the non-visible region are described therein (bone defects, root canal), which as a result can, in addition, only be produced in self-curing manner in the form of a two-component material.

Within the scope of the invention the expression 'dental material' denotes materials for the filling of teeth, inlays or onlays, attachment cements, glass-ionomer cements, compomers, facing materials for crowns and bridges, materials for artificial teeth, in dentine bondings, lining materials, root-filling materials or other materials for prosthetic, conservative and preventive dentistry. In particular, the term 'dental material' also includes composites for applications in the fields of medical and technical dentistry, sealant materials, self-curing composites, stump-reconstruction materials, facing synthetics, highly filled and normally filled dual cements and also normally filled tooth lacquers containing fluoride.

By way of binding agent for the dental material all those binding agents based on a polymerisable, ethylenically unsaturated monomer come into consideration that are familiar to the person skilled in the art for this application. The polymerisable monomers that can be used successfully preferably include those having acrylic and/or methacrylic groups.

In this connection it is a matter in particular of, inter alia, esters of a-cyanoacrylic acid, (meth)acrylic acid, urethane (meth)acrylic acid, crotonic acid, cinnamic acid, sorbic acid, maleic acid and itaconic acid with monohydric or dihydric alcohols; (meth)acrylamides such as, for example, N-isobutyl acrylamide; vinyl esters of carboxylic acids such as, for example, vinyl acetate; vinyl ethers such as, for example, butyl vinyl ether; mono-N-vinyl compounds such as N-vinyl pyrrolidone; and styrene as well as its derivatives. Particularly preferred are the monofunctional and polyfunctional (meth)acrylic esters and urethane (meth)acrylic esters listed below.

(a) Monofunctional (meth)acrylates

Methyl (meth)acrylate, n- or i-propyl (meth)acrylate, n-, i- or tert.-butyl (meth)acrylate and 2-hydroxyethyl (meth)acrylate.

(b) Difunctional (meth)acrylates

Compounds of the general formula:

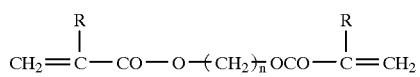

in which R is hydrogen or methyl and n is a positive integer between 3 and 20, such as, for example, di(meth)acrylate of propanediol, butanediol, hexanediol, octanediol, nonanediol, decanediol and eicosanediol, compounds of the general formula:

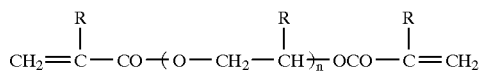

in which R is hydrogen or methyl and n is a positive integer between 1 and 14, such as, for example, di(meth)acrylate of ethylene glycol, diethylene glycol, triethylene glycol, tetraethylene glycol, dodecaethylene glycol, tetradecaethylene glycol, propylene glycol, dipropyl glycol and tetradecapropylene glycol; and glycerine di(meth)acrylate, 2-2'-bis[p-(γ-methacryloxy-β-hydroxypropoxy)phenylpropane] or bis-GMA, bisphenol A dimethacrylate, neopentyl glycol di(meth)acrylate, 2,2'-di(4-methacryloxypolyethoxyphenyl) propane having 2 to 10 ethoxy groups per molecule and 1,2-bis(3-methacryloxy-2-hydroxypropoxy)butane.

(c) Trifunctional or multifunctional (meth)acrylates

Trimethylolpropane tri(meth)acrylates and pentaerythritol tetra(meth)acrylate.

(d) Urethane (meth)acrylate

Conversion products of 2 mol (meth)acrylate monomer containing hydroxyl groups with one mol diisocyanate and conversion products of a urethane prepolymer comprising two NCO terminal groups with a methacrylic monomer comprising a hydroxyl group, such as are represented, for example, by the following general formula:

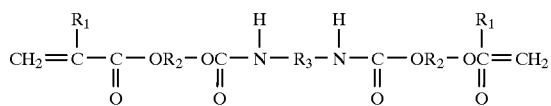

in which R signifies hydrogen or a methyl group, $R_2$ represents an alkylene group and $R_3$ represents an organic residue.

The stated monomers are used either on their own or in the form of a mixture of several monomers.

Monomers that are used to quite particular advantage in the dental material according to the invention include, above all, 2,2-bis-4(3-methacryloxy-2-hydroxypropoxy) phenylpropane (bis-GMA), 3,6-dioxaoctamethylene dimethacrylate (TEDMA) and/or 7,7,9-trimethyl-4,13-dioxo-3,14-dioxa-5,12-diaza-hexadecane-1,16-dioxy dimethacrylate (UDMA).

Depending on the type of catalyst employed, the dental material may be polymerisable when hot or cold and/or may be polymerisable by means of light. By way of catalysts for hot polymerisation, use may be made of the known peroxides such as dibenzoyl peroxide, dilauroyl peroxide, tert.-butyl peroctoate or tert.-butyl perbenzoate, but α,α'-azo-bis (isobutyroethyl ester), benzopinacol and 2,2'-dimethylbenzopinacol are also suitable.

By way of catalysts for photopolymerisation, use may be made, for example, of benzophenone and its derivatives, as well as benzoin and its derivatives. Other preferred photosensitizers are α-diketones such as 9,10-phenanthrenequinone, diacetyl, furil, anisil, 4,4'-dichlorobenzil and 4,4'-dialkoxybenzil; use of camphor quinone is particularly preferred. Use of the photosensitizers together with a reducing agent is preferred. Examples of reducing agents are amines such as cyanethylmethylaniline, dimethylaminoethyl methacrylate, triethyl amine, triethanol amine, N,N-dimethylaniline, N-methyldiphenyl amine, N-N-dimethyl-sym.-xylidine and N,N-3,5-tetramethylaniline and 4-dimethylaminoethyl benzoate.

By way of catalysts for cold polymerisation, use is made of systems that supply radicals, for example benzoyl peroxide or lauroyl peroxide together with amines such as N,N-dimethyl-sym.-xylidine or N,N-dimethyl-p-toluidine. Use may also be made of dual-curing systems for the purpose of catalysis, for example photoinitiators with amines and peroxides. By way of photocatalysts, mixtures of catalysts that cure in UV light and catalysts that cure within the range of visible light also come into consideration.

The quantity of these catalysts in the dental material customarily amounts to between 0.01 and 5 wt-%.

The dental material according to the invention preferably serves as tooth-filling material. Tooth-filling materials are also produced in the form of two-component materials that cure in the cold state after mixing. The composition is similar to that in the case of the light-curing materials, only instead of the photocatalysts, benzoyl peroxide, for example, is worked into one paste and N,N-dimethyl-p-toluidine, for example, is worked into the other paste. By mixing roughly equal parts of the two pastes a tooth-filling material is obtained that cures within a few minutes.

If in the case of the last-named materials the amine is omitted and by way of catalyst use is made, for example, of benzoyl peroxide only, a heat-curing dental material is obtained that can be used for the production of an inlay or of artificial teeth. For the production of an inlay, an impression of the cavity is taken in the mouth of the patient and a plaster model is produced. The paste is introduced into the cavity of the plaster model and the whole is polymerised under heat in an autoclave. The inlay is taken out, machined, and then cemented into the cavity in the mouth of the patient.

Filler A) is an essential and characteristic constituent of the dental material according to the invention.

In the case of filler A) it is, in each instance, a matter of at least one so-called mixed apatite. In this connection the term 'mixed apatite' denotes a chemical mixture of two or three apatites—that is to say, two or three have a common crystal lattice.

The effect that is striven for, inter alia, in accordance with the invention, namely the exchange of ions with the biological environment of the dental material, with simultaneously high transparency and hardness of the dental material, can be achieved by various types of mixed apatite.

For instance, the invention can be realised by means of filled dental materials that comprise mixed apatites of type A1) or type A2) or type A3). Also successful are filler mixtures A) that comprise two or more mixed apatites of type A1), type A2) or type A3). In addition, not only mixtures of two or more apatites of the same type (A1), A2) or A3)) but also mixtures having two or more mixed apatites can be used successfully in which the various mixed apatites employed pertain to different types A1), A2) and/or A3).

For instance, the invention encompasses, inter alia, filled dental materials that comprise by way of fillers of type A), for example,
one mixed apatite of type A1),
two mixed apatites of type A1),
three mixed apatites of type A1),
one mixed apatite of type A2),
two mixed apatites of type A2),
three mixed apatites of type A2),
one mixed apatite of type A3),
two mixed apatites of type A3),
three mixed apatites of type A3),
one mixed apatite of type A1) and one mixed apatite of type A2),
one mixed apatite of type A1) and one mixed apatite of type A3),
one mixed apatite of type A2) and one mixed apatite of type A3),
one mixed apatite of type A1) and two mixed apatites of type A2),
one mixed apatite of type A1) and two mixed apatites of type A3),
one mixed apatite of type A2) and two mixed apatites of type A3)
two mixed apatites of type A2) and one mixed apatite of type A3),
two mixed apatites of type A1) and one mixed apatite of type A2),
two mixed apatites of type A1) and one mixed apatite of type A3), or
one mixed apatite of type A1), one mixed apatite of type A2) and one mixed apatite of type A3).

The mixed apatites of type A1) correspond to the general formula I

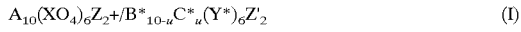  (I)

in which
A and B* are the same or different and stand for a bivalent cation and/or a charge-equivalent combination of monovalent and trivalent cations, whereby the cations have ionic radii within the range 0.069–0.174 nm,
X signifies a cation of valency three, four, five or six, whereby the cations have ionic radii within the range 0.026–0.056 nm,
Y* signifies $(SO_4)^{2-}$ and/or $(PO_3F)^{2-}$, optionally with a proportion of up to ⅙, relative to molar quantities, $(CO_3)^{2-}$,
Z and Z' are the same or different and stand for $F^-$, $Cl^-$, $OH^-$ or $O^{2-}$, and
C* is a monovalent cation, preferably $Na^+$, and also
u is an integer or fraction within the range from 0 to 6 and specifies the degree of substitution of B* by C* in the cation sublattice.

By reason of the general formula I and also the explanation with regard to what the term 'mixed apatites' signifies within the scope of the invention it is self-evident that in formula I either A differs from B* and/or $XO_4$ differs from Y* and/or Z differs from Z'. In formula I, for reasons of comprehension the composition of the mixed apatite is specified in such a way that the composition of the one apatite $A_{10}(XO_4)_6Z_2$ and also of the other apatite $B^*_{10-u}C^*_u(Y^*)_6Z'_2$ involved in the synthesis of the mixed apatite remains clearly apparent.

Instead of the pure apatite $A_{10}(XO_4)_6Z_2$, mixed apatites of the formulae

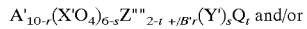 and/or

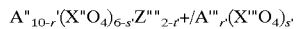

may also be contained in the mixed apatite of type A1). In this way one arrives formally at the mixed apatites of types A2) (general formula II) and A3) (general formula III),

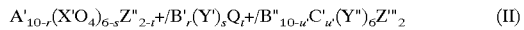  (II)

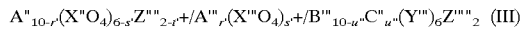  (III)

in which
A', A'', A''', B', B'' and B''' are the same or different and stand for a divalent cation and/or a charge-equivalent combination of monovalent and trivalent cations, whereby the cations have ionic radii within the range 0.069–0.174 nm,
X', X'' and X''' independently of one another are the same or different and stand for a cation of valency three, four, five and/or six, whereby the cations have ionic radii within the range 0.026–0.056 nm,
Y', Y'' and Y''' independently of one another are the same or different and signify $(SO_4)^{2-}$ and/or $(PO_3F)^{2-}$, optionally with a proportion of up to ⅙, relative to molar quantities, $(CO_3)^{2-}$,
Q, Z'', Z''', Z'''' and Z''''' independently of one another are the same or different and stand for $F^-$, $Cl^-$, $OH^-$ or $O^{2-}$,
and C' and C'' independently of one another are the same or different and are a monovalent cation, and also
u' and u'' independently of one another are the same or different and are an integer or fraction within the range from 0 to 6 and specify the degree of substitution of B'' by C' and of B''' by C'' in the respective cation sublattice,
r is an integer or fraction within the range from 0 to 10 and specifies the degree of substitution of A' by B' in the cation sublattice, r' is an integer or fraction between 0 and 9 and specifies the degree of substitution of A'' by A''',
s and s' independently of one another are the same or different and are an integer or fraction within the range from 0 to 6 and specify the degree of substitution of $X'O_4$ by Y' and of $X''O_4$ by $X'''O_4$ in the respective sublattice of the tetrahedral anions, and
t and t' independently of one another are the same or different and are an integer or fraction within the range from 0 to 2 and specify, respectively, the degree of substitution of Z'' by Q and unoccupied lattice positions for type A3).

Also in the case of the apatites of type A2) and A3) (general formulae II and III, respectively) it is again the case that the chosen notation is intended to make clear of which individual apatites the crystal lattice of the particular mixed apatite may be imagined to be composed.

In an expedient refinement the dental material comprises mixed apatites of type A1), A2) and/or A3) in which A, A', A″, A‴, B*, B′, B″ and/or B‴ are the same or different and are $Mg^{2+}$, $Ca^{2+}$, $Sr^{2+}$, $Ba^{2+}$, $Y^{2+}$, $Ti^{2+}$, $Zr^{2+}$, $Mn^{2+}$, $Fe^{2+}$, $Pd^{2+}$, $Cu^{2+}$, $Ag^{2+}$, $Zn^{2+}$, $Sn^{2+}$, $RE^{3+}$, $RE^{3+}$, $Al^{3+}$, $In^{3+}$, $Y^{3+}$, $Na^+$ and/or $K^+$.

In this connection RE stands for rare-earth metals.

In particular it has also been shown within the scope of the invention that in the case of incorporation of certain cations into the mixed apatites according to the invention an antimicrobial effect can be achieved. Particularly expedient in this context is the incorporation of $Cu^{2+}$, $Ag^{2+}$, $Zn^{2+}$ and/or $Sn^{2+}$.

In this connection the solution, in accordance with the invention, of incorporation into the mixed apatite is clearly more favourable than the previously known possibility of attaching microbially active means onto apatites, as is known, for example, from DE 39 32 469.

Furthermore, with respect to the dental material according to the invention it is preferred if it comprises fillers A) in which X, X′, X″ and/or X‴ are the same or different and are $B^{3+}$, $Al^{3+}$, $Si^{4+}$, $P^{5+}$ and/or $S^{6+}$.

In another expedient embodiment the dental material of the invention is characterised by fillers A) in which C, C′ and/or C″ signify $Na^+$.

According to the invention the fillers A1), A2) and/or A3) are contained in the dental material in a quantity that is sufficient to permit an exchange of ions with the biological environment. It is advantageous if the proportion by weight of filler A) amounts to between 1 and 70 wt-%, relative to the dental material. Particularly expedient is a modification in which the proportion by weight of filler A) amounts to between 2 and 35 wt-%, relative to the total weight of the dental material. It proves to be quite particularly favourable if the proportion by weight of filler A) amounts to between 2 and 7 wt-%, relative to the dental material.

Within the bounds of these quantities it is possible for the refractive index of the dental material to be adjusted in purposeful manner over a relatively wide diversity of compositions and quantities. In a preferred embodiment said dental material is characterised in that the refractive index of filler component A) lies within the range from 1.50 to 1.66. This can be achieved, for example, by use being made of mixed apatites of type A1) in which pure fluorapatite can be imagined as $A_{10}(XO_4)_6Z_2$, the refractive index of which amounts to around 1.63, whereby $Ca_4Na_6(SO_4)_6F_2$ (refractive index 1.52) or $Ca_6Na_4(PO_3F)_6O_2$ (refractive index 1.52) are involved as apatites of type $B^*_{10-u}C^*_u(Y^*)_6Z'_2$ in the structure of the mixed apatite for the purpose of adjusting and lowering the refractive index.

The particle size of the fillers A) to be used in accordance with the invention in the dental material is non-critical over wide ranges. The invention is preferably characterised in that the particle size of filler component A) lies within the range from 0.01 to 10 μm.

The production of the apatites is effected in a manner familiar to the person skilled in the art, for example by solid-state reaction in accordance with processes that are known from the literature (see, for example, A. G. Cockbain: Miner. Mag. 1968, 36, 654).

For example, for a mixed apatite consisting of type Al) corresponding to the reaction equation 9 $Ca_3(PO_4)_2$+3 $CaSO_4$+3 $Na_2SO_4$+4 $CaF_2$→4 $Ca_{8.5}Na_{1.5}(PO_4)_{4.5}(SO_4)_{1.5}F_2$, a refractive index of $n_D$=1.58±0.01 results. Alternatively, a mixed apatite can be produced by sintering the pure terminal members together.

As a result of variation of the educts, mixed apatites having a refractive index between 1.63 and 1.52 can be adjusted in this way.

Overall it can be said that the mixed apatites according to the invention are based on $SO_4^{2-}$ and $PO_3F^{2-}$ anions which may comprise a subordinate proportion, namely up to ⅙ of the molar quantities, of $CO_3^{2-}$ anions.

On account of its planar structure, $(CO_3)^{2-}$ is only suitable to a very limited extent for the substitution of tetrahedral phosphate groups. Consequently the possibilities of influence with a view to lowering the refractive index of phosphate apatites are only slight. In contrast, with the tetrahedral sulphate or monofluorophosphate ion a total replacement of the phosphate groups is possible, with a correspondingly large influence on the refractive indices of the modified mixed apatites.

In addition, the fillers may also be used in silanised form. As a result, a better integration into the polymer matrix is achieved.

Besides the essential and characteristic filler component A), the dental material may comprise further fillers B) and C) by way of optional but nonetheless very advantageous and no less preferred components.

Consequently, in yet another preferred embodiment the invention is characterised in that in a mixture with component A) the dental material comprises by way of filler component B)

B1) aspherical, fragmented powders consisting of quartz, glass ceramic and/or glass having a refractive index from 1.46 to 1.58 and an average particle size from 0.5 to 5.0 μm and/or B2) microscopic beads and/or B3) inorganic fibres and/or B4) organic fibres.

In this connection the weight ratio of A) to B) is preferably within the range from 10:1 to 1:30.

In the case of the inorganic filler B1) of the filler mixture it is a matter of quartz powder, glass-ceramic powder or glass powder. Use is preferably made of glasses. The average primary-particle size of the inorganic filler B1) should lie between 0.5 and 5.0 μm, in particular between 1.0 and 2.0 μm and most preferably between 1.0 and 1.5 μm, whereas the refractive index should exhibit values between 1.50 and 1.58, in particular between 1.52 and 1.56. Use may also be made of filler mixtures. In accordance with the invention use is preferably made of Ba-silicate glasses having an average grain size within the range from 1.1 to 1.3 μm, and also of Sr-silicate glasses having an average grain size within the range from 1.1 to 1.3 μm, and also of Li/Al-silicate glasses having an average grain size from 1.0 to 1.6 μm. Such powders may, for example, be obtained by fine grinding with a conventional ultrafine grinder.

By way of fragmented fillers of type B) there also come into consideration

B5) polysiloxane fillers that are aluminiferous and consist of units corresponding to the formula

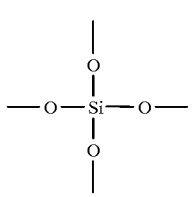

(I′)

and units corresponding to the formula

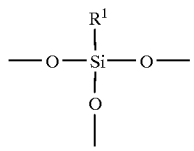
(II')

wherein $R^1$ stands for a linear or branched alkyl group combined with an acrylate or methacrylate residue and having 1 to 6 C atoms, or for a singly olefinically unsaturated linear or branched hydrocarbon residue having 2 to 8 C atoms or for a cyclic, singly olefinically unsaturated hydrocarbon residue having 5–8 C atoms or for a linear or branched alkyl group having 1 to 8 C atoms, a cycloalkylene group having 5 to 8 C atoms, a phenyl group or an alkylaryl group, and/or units corresponding to the formula

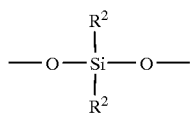
(III')

in which $R^2$ represents a methyl, ethyl, propyl or phenyl group and—in each of the compositions—units are present corresponding to the formula

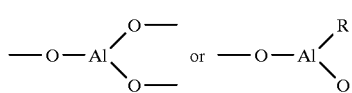
(IV')

in which $R^3$ is a linear or branched alkyl group having 1 to 5 C atoms or a phenyl group and the free valencies of the oxygen atoms bonded to the silicon and aluminium atoms in the case of the units (I'), (II') and/or (III') and also (IV') as in the case of heterosiloxane skeletons are saturated by a silicon atom of a similar or a different unit or by an aluminium atom, whereby the ratio of the silicon atoms from the units corresponding to formula (I') to the sum of the silicon atoms of the units (II') and (III') amounts to between 3:1 and 100:1 and the ratio of the sum of the silicon atoms from the units (I'), (II') and (III') to the aluminium atoms from the units (IV') amounts to between 2:1 and 200:1.

In this connection the aluminium in the polysiloxane filler may also optionally be replaced by a different metal.

Other fillers of type B) are, inter alia, B2) microscopic beads such as are described, for example, in DE-A 32 47 800, B3) inorganic fibres, B4) organic fibres. These may be employed on their own, in a mixture of two or more and/or together with quartz powders, glass-ceramic powders or glass powders B1) or polysiloxane fillers of type B5)

The fillers B2) include, inter alia, an amorphous, globular material based on silicon dioxide, which in addition also contains an oxide of at least one metal pertaining to Groups I, II, III and IV of the Periodic Table. Use is preferably made of strontium oxide and/or zirconium oxide. The average primary-particle size lies within the range from 0.1 to 1.0 μm, in particular around 0.15 to 0.5 μm. The refractive index of the inorganic filler B2) lies between 1.50 and 1.58, in particular between 1.52 and 1.56. A particularly preferred value is 1.53±0.01. Also possible are filler mixtures, provided that they satisfy the parameters with regard to particle size and refractive index. The filler of type B2) may also be present in sintered form as a mixture of agglomerates having an average particle size from 1 to 30 μm.

The fillers B3) include, inter alia, glass fibres, glass-fibre gauzes, which are optionally sintered, aluminium-oxide fibres and the like.

The fillers B4) include, inter alia, polyethylene fibres and carbon fibres.

In another advantageous variant the dental material of the invention is characterised in that, besides filler A), by way of filler C) in the finished, completely polymerised dental material it comprises globular particles based on $SiO_2$ consisting of C1) a spherical, polydisperse and/or monodisperse $SiO_2$ nucleus which is coated at individual points on its surface with metal-oxide particles, whereby the coated particles exhibit a refractive index from 1.45 to 1.62 and an average primary-particle size from 0.005 to 2 μm and the coating particles consisting of metal oxide have an average size of less than 60 nm, and/or C2) $SiO_2$ having a refractive index between about 1.38 and <1.50 and an average primary-particle size from about 0.04 μm to 1.5 μm, and/or C3) an $SiO_2$ nucleus which is coated with an oxide of at least one-element pertaining to Groups I, II, III and IV of the Periodic Table, whereby the coated particles exhibit a refractive index from 1.45 to 1.62 and an average primary-particle size from 0.04 to 1.5 μm and the coating is between about 15 and 40 nm thick, and/or C4) particles described under C1), C2) or C3) which in addition are covered with a layer consisting of a polymerisable organic binding agent based on monofunctional or multifunctional (meth)acrylates and/or reaction products of isocyanates and methacrylates that contain OH groups, whereby the primary-particle size of the particles that are provided with a polymerisable layer of binding agent amounts to between about 0,04 and 1.5 μm, whereas the layer thickness of the covering layer lies within the range from 5 nm to 50 nm and the refractive index of the coated particles lies within the range 1.40–1.52.

In this connection the weight ratio of A) to C) preferably lies within the range from 10:1 to 1:30.

A filler C1) to be employed in the dental material according to the invention is based on pure $SiO_2$ particles. From the latter the $SiO_2$ particles which are coated at special surface locations can then be obtained.

The $SiO_2$ initial particles are polydisperse or monodisperse and may also be present in the form of a mixture of polydisperse and monodisperse spheres.

The $SiO_2$ initial particles are preferably monodisperse, non-porous and essentially globular. In principle all oxide particles are suitable which may be obtained by hydrolytic polycondensation from alcoholate compounds of corresponding elements and which in this connection accumulate in the form of monodisperse compact spherical particles. The basic reaction conditions for the production of $SiO_2$ particles by hydrolytic polycondensation can be gathered, for example, from the following publications: W. Stöber et al. in J. Colloid and Interface Science 26, 62 (1968) and 30, 568 (1969), and also U.S. Pat. No. 3,634,588.

For the production of highly monodisperse, non-porous globular $SiO_2$ particles that exhibit a standard deviation of no more than 5%, reference is made to EP 0 216 278, which discloses a correspondingly geared production process based on hydrolytic polycondensation. The core of this process, which is quite particularly preferred for the production of the $SiO_2$ particles according to the present invention, is a two-stage procedure. In this connection, firstly by means of hydrolytic polycondensation of tetraalkoxysilanes in aqueous-alkaline-ammoniacal medium a sol or a suspension of primary particles is formed which is brought to the desired final size directly afterwards by dosed addition of further tetraalkoxysilane.

An analogous process for the production of various metal oxides in the form of spherical particles having a narrow particle-size distribution is likewise to be gathered from EP 0 275 688.

Spherical $SiO_2$ particles coated at individual locations or points with particles consisting of metal oxide, in the case of which the "coated" particles exhibit a refractive index within the range from 1.45 to 1.62 and an average primary-particle size from 0.005 to 2 μm and the coating particles have an average particle size of less than 60 nm, can be obtained, for example, by highly monodisperse, non-porous, spherical $SiO_2$ particles having a standard deviation of no more than 5% being dispersed at a temperature within the range 50–90° C. in a concentration of 1 to 30 per cent by weight in de-ionised water, by an aqueous, 5 to 40 per cent by weight, metal-salt solution, preferably titanium-salt solution, having a pH value within the range from 1.3 to 2.5 and a rate of addition within the range from 0.0005 to 5 mg metal oxide, preferably $TiO_2$, per minute and per $m^2$ of surface of the $SiO_2$ particles being added while the pH value is maintained within the specified range by addition of a base, by the $SiO_2$ particles coated in such a manner being separated, washed with water and then with alcohol, preferably ethanol, dried firstly in contact with the air and then in a vacuum at temperatures within the range from about 70 to 125° C. and optionally calcined.

Alternatively, spherical $SiO_2$ particles which can be used in the dental material according to the invention by way of filler component C1) and which exhibit at individual points or locations on their surface a coating with metal-oxide particles, whereby the coating particles consisting of metal oxide have in the coated particle an average particle size of less than 60 nm, with a refractive index within the range from 1.45 to 1.62 and an average primary-particle size within the range from 0.005 to 2 μm, can also be obtained by an aqueous solution of a metal halide, preferably titanium tetrachloride, being heated to about 60° C. subject to stirring, by the metal-oxide suspension obtained, in the preferred case the $TiO_2$ suspension, being added dropwise to a suspension of spherical $SiO_2$ particles (obtainable as described above), by the pH value being adjusted with concentrated, preferably 32-%, NaOH solution subject to stirring to about 2.0, by a silane coupling agent being added to the suspension, by the pH value being raised after about 15 minutes with concentrated NaOH to about 8.0, by the suspension being stirred for a further 10 minutes, by the $SiO_2$ particles that have been filtered off, washed and dried being pulverised with a mixing device and by the powder obtained being calcined at 700° C. for 5 minutes.

The primary-particle size of the spherical $SiO_2$ particles which are coated at individual locations and which serve as filler C1) lies, with respect to the dental materials according to the invention, conventionally within the range between 0.005 and 2 μm. A size of the primary particles—ie, of the $SiO_2$ beads underlying the coated $SiO_2$ spheres—from about 0.05 to 0.5 μm is preferred. Quite particularly preferred in the sense of the invention is a primary-particle size from 0.1 to 0.5 μm. Also expedient for certain dental applications, however, is the range from 0.01 to 2 μm, preferably from 0.05 to 0.15 μm.

Coated $SiO_2$ particles are obtainable, inter alia in accordance with the described processes, in the case of which the coating particles are oxides of at least one element pertaining to Groups I, II, III and/or IV of the Periodic Table. Of these, oxides pertaining to Group IV of the Periodic Table are preferred. Expedient are, above all, oxides of titanium or zirconium. But also possible are oxides from the iron group, just as oxides from the group of the lanthanides may be advantageous. But the fillers C1) also prove to be particularly favourable when the oxides are $TiO_2$, $Fe_2O_3$ and/or $ZrO_2$.

Regarded overall, a coating with $TiO_2$ has proved to be extremely good.

In particular, the choice of the metal oxide that is employed for the coating permits, inter alia, selective influencing and adjustment of the refractive index of the filler C1) and hence also adaptation to the refractive index of the overall dental material.

The size of the metal-oxide particles, preferably of the $TiO_2$, $Fe_2O_3$ and $ZrO_2$ particles, in the filler C1) lies within the range below 60 nm. The average particle size of the metal-oxide particles that are present in the manner of a coating at individual locations on the surface of the $SiO_2$ primary particles preferably amounts to between 0.0005 and 50 nm.

Within the scope of the invention the proportion of the metal oxides in the fillers C1) amounts to between about 20 and 75 per cent by weight, preferably between 40 and 50 per cent by weight, in each case relative to the total weight of the filler C1). In a particularly advantageous refinement of the invention the dental material is characterised, in accordance with the invention, in that in the case of the particles C1) the weight ratio of coating particle consisting of metal oxide to nucleus consisting of $SiO_2$ lies within the range from 1:4 to 3:1, in particular within the range from 1:2 to 2:1.

In an expedient embodiment the particles C1) with a structured surface exhibit a specific surface of >150 $m^2/g$ (BET) and also an average pore size of 5 nm. They may, as described below, be silanised in a form that is conventional for dental materials.

Furthermore it is possible to subject the filler C1) consisting of $SiO_2$ spheres and metal-oxide particle coating to aftercoating. To this end, organic or inorganic substances are employed in accordance with methods that are known as such. As a result of the aftercoating it becomes possible to avoid, in still more reliable manner, a possible agglomeration of the monodisperse particles during the drying process.

In a particular embodiment the dental material is characterised in that the particles C1) are subjected to aftercoating with silanes of the general formula $RSi(OX)_3$ in which R is an alkyl group having 1 to 18 C atoms and X is an alkyl group having 1 or 2 C atoms, and/or with metal oxides. If, for the purpose of aftercoating, use is made of a silane, it is expedient if this is applied in a quantity of about 0.02 to 2 per cent by weight of silane, reckoned as $SiO_2$, relative to the weight of the particles C1). Similarly, the fillers A) may also be silanised. If metal oxides are employed for the aftercoating, then this is effected in a quantity of 1 to 100 per cent by weight, preferably 10 per cent by weight, relative to the metal-oxide content of the particles Cl) that have not been subjected to aftercoating.

Particularly advantageous aftercoating agents include, inter alia, $CH_3Si(OMe)_3$, $TiO_2$, $Fe_2O_3$ and/or $ZrO_2$.

Also expedient is an embodiment in which the particles Cl) are additionally covered with a layer consisting of a polymerisable organic binding agent based on monofunctional or multifunctional (meth)acrylates and/or reaction products of isocyanates and methacrylates that contain OH groups, whereby the primary-particle-size of the particles that are provided with a polymerisable layer of binding agent amounts to between about 0.04 and 1.5 μm, whereas the layer thickness of the covering layer lies within the range from 5 nm to 50 nm and the refractive index of the coated particles lies within the range 1.40–1.52.

By way of fillers C) there also come into consideration, besides the fillers C1), the variants C2) to C4), on their own or in admixture to C1), or also arbitrary mixtures of C1), C2), C3) and/or C4).

It therefore conforms to a preferred refinement of the dental material according to the invention if said material comprises, besides the particles C1), by way of filler component C) particles consisting of C2) $SiO_2$ with a refractive index between about 1.38 and <1.50 and an average primary-particle size from about 0.04 μm to 1.5 μm, C3) an $SiO_2$ nucleus which is coated with an oxide of at least one element pertaining to Groups I, II, III and IV of the Periodic Table, whereby the coated particles exhibit a refractive index from 1.45 to 1.62 and an average primary-particle size from 0.04 to 1.5 μm and the coating is between about 15 and 40 nm thick, and/or C4) particles described under C1), C2) or C3) which in addition are covered with a layer consisting of a polymerisable organic binding agent based on monofunctional or multifunctional (meth)acrylates and/or reaction products of isocyanates and methacrylates that contain OH groups, whereby the primary-particle size of the particles that are provided with a polymerisable layer of binding agent amounts to between about 0.04 and 1.5 μm, whereas the layer thickness of the covering layer lies within the range from 5 nm to 50 nm and the refractive index of the coated particles lies within the range 1.40–1.52.

Common to components C2) to C4) in this connection is, in particular, the fact that all types are based on $SiO_2$ or consist exclusively thereof and furthermore all components C2) to C4) are present not in the form of an agglomerate but rather in the form of separate particles in the completely polymerised dental material, just like component C1).

In accordance with the invention there may be employed as component C2), for example, $SiO_2$ particles having a refractive index between 1.38 and <1.50 and having an average primary-particle size from about 0.04 μm to about 1.5 μm by way of component C), preferably together with C1).

In a preferred embodiment according to the invention the pure $SiO_2$ particles that can be admixed to the filler by way of component C2) exhibit an average particle diameter from about 0.04 μm to about 0.25 μm. This particular size is suitable, above all, in dental materials that find application, in particular, in connection with filling materials, facing materials or artificial teeth.

Also for these applications in particular it is particularly expedient that the average particle size of the pure $SiO_2$ particles is not greater than 0.1 μm overall.

In those cases where the transparency of the material is of subordinate importance (for example in the case of stump-reconstruction materials, cements for attachment, sealants and the like), particle sizes from 0.25 μm to 1.5 μm are also preferred. In particularly expedient manner the particles are then present in a size ranging from 0.25 to 1.0 μm.

The pure $SiO_2$ particles to be used in accordance with the invention by way of component C2) are preferably monodisperse, non-porous and essentially globular. In principle, all oxide particles are suitable which may be obtained by hydrolytic polycondensation from alcoholate compounds of corresponding elements and which in this connection accumulate in the form of monodisperse compact spherical particles. The basic reaction conditions for the production of $SiO_2$ particles by hydrolytic polycondensation are described in the reference specified above.

For the production of highly monodisperse, non-porous globular $SiO_2$ particles that exhibit a standard deviation of no more than 5%, reference is likewise made to the sources already cited above.

In the case of the fillers of type C3), within the scope of the invention it is a matter of stratiform particles that comprise an $SiO_2$ nucleus which is coated with an oxide of at least one element pertaining to Groups I, II, III and IV of the Periodic Table.

In this connection the $SiO_2$ particle used by way of nucleus may in principle be identical to the pure $SiO_2$ particle described under C2), as a rule, however, as initial product it exhibits a particle size that is reduced by the thickness of the coating. It is essential to emphasise that, in accordance with the invention, the particles of type C3) are not present in the form of mixed-oxide particles, but rather the $SiO_2$ nucleus is surrounded by an appropriate different oxide of at least one element pertaining to Groups I to IV of the Periodic Table. Surprisingly it has turned out that, in contrast to the mixed oxides, the coated particles are, as a rule, present separately in the completely polymerised dental material and in particular not in aggregated form. The coated particles of type C3) may in principle be produced by analogy with the two-stage processes described herein under C2). In this connection, in the course of the hydrolytic polycondensation of tetraalkoxysilane in aqueous-alkaline-ammoniacal medium a sol or a suspension of primary particles is formed which is brought to the desired final size directly afterwards by dosed addition of another tetraalkoxysilane. In this way a primary particle consisting of an oxide is formed, onto which a different oxide or an oxide mixture is then deposited in the growth step. By this means the resulting refractive index can be varied advantageously. If the quantity of the oxide formed in the growth stage were to predominate in the finished particle it would be substantially responsible for the resulting refractive index. The particularly preferred oxidic compounds pertaining to Groups I to IV of the Periodic Table that are deposited onto the $SiO_2$ nucleus include, inter alia, $TiO_2$, $ZrO_2$, $Al_2O_3$ and/or $V_2O_5$. In this connection $TiO_2$ is quite particularly preferred, whereby in the course of the use thereof care should be taken to ensure that the $TiO_2$ is completely bonded, since otherwise in certain circumstances yellow colorations of the dental material may occur. Besides the preferred compounds from Groups I to IV of the Periodic Table, other compounds are also possible. For instance, $Nb_2O_5$ or mixed systems with the aforementioned oxides from Groups I to IV of the Periodic Table can also be successfully deposited onto $SiO_2$ primary particles.

In accordance with the invention the particles described under C1), C2) or C3) may be additionally covered with a layer consisting of a polymerisable organic binding agent (filler C4)) based on monofunctional or multifunctional methacrylates and/or reaction products of isocyanates and methacrylates that contain OH groups. By this means an organic modification of the particles on the surface is possible which in certain circumstances is advantageous for the particular application. This may be undertaken in full accordance with methods such as are known for the production of silica gels that are customary as chromatographic sorbents. Common modifying agents in this connection are organotrialkoxysilanes such as, for example, methyltriethoxysilane, ethyltriethoxysilane, octyltriethoxysilane, octadecyltriethoxysilane, monofluoroalkylethoxysilane or polyfluoroalkylethoxysilane or also silanes having functionalised organic groups that enable a subsequent further modification by covalent bonding attachment in known manner. In the latter case, with regard to the use in accordance with the invention of the particles by way of fillers in polymeric or polymerisable systems those organotrialkoxysilanes are preferred which comprise such functional groups with which covalent integration into the polymer material can be achieved. Examples of these are trimethoxyvinylsilane, triethoxyvinylsilane and 3-glycidoxypropyltrimethoxysilane, and also silanes having inorganic residues bearing hydroxyl, carboxyl, epoxy and carboxylic-ester groups. The integration into the dental material of the particles according to A4) that have been modified in such a manner is effected in this connection by working the particles into the dental material and by subsequent polymerisation in the course-of the actual curing of the dental material.

Alternatively it is also possible to polymerise the surface-modified particles according to C1), C2) or C3) prior to actually working them into the dental material. This can be effected, for example, in accordance with a process described in the Journal of Colloid and Interface Science 160, 298–303 (1993). In every case, as a result of suitable coordination of the monomer that is employed for the surface modification with the monomer or the monomer mixture that forms the polymer matrix of the dental material, a fine graduation and regulation of the refractive index of the overall dental material can be achieved.

Optionally, still other fillers (D) may be employed with a view to achieving an increased X-ray opacity, whereby the average primary-particle size of said fillers should not exceed 5.0 $\mu$m. Such fillers are described, for example, in DE-OS 35 02 594.

Optionally, with a view to adjusting the viscosity, small amounts of microfine, pyrogenic or wet-precipitated silicic acid (filler (E)) may be worked into the dental material, but at most 50 wt-%, relative to the dental material. Preferred amounts are 5–25 wt-%, particularly preferred amounts are 5–12 wt-%.

Within the scope of the invention it is furthermore expedient to adjust the ratio of filler B) to filler C) in the finished dental material in such a way that an aggregation of the fillers (C) is avoided. This should be ascertained empirically by the person skilled in the art by means of appropriate experiments.

In a particularly preferred embodiment the ratio of the filler components (C) to the fillers (B) is adjusted within the range from 1:85 to 4:1 (in each case in terms of wt-%) in such a way that the strength of the resulting dental material, in terms of its compressive strength, lies within the range from >320 to about 480 MPa. In this connection it has proved particularly favourable if the ratio of fillers C) to fillers B) amounts to $\geq$1:10 (in each case in terms of wt-%).

Also a subject of the invention is the use of one or more mixed apatites of the type A1) $A_{10}(XO^-_4)_6Z_2 +/B^*_{10-u}C^*_u(Y^*)_6Z'_2$ and/or A2) $A'_{10-r}(X'O_4)_{6-s}Z''_{2-t} +/B'_r(Y')_sQ_t +/B''_{10-u'}C'_{u'}(Y'')_6Z'''_2$ and/or A3) $A''_{10-r'}(X''O_4)_{6-s'}Z''''_{2-t'} +/A'''_{r'}(X'''O_4)_{s'} +/B'''_{10-u''}C''_{u''}(Y''')_6Z''''_2$ in which A, A', A'', A''', B*, B', B'' and B''' are the same or different and stand for a bivalent cation and/or a charge-equivalent combination of monovalent and trivalent cations, whereby the cations have ionic radii within the range 0.069–0.174 nm, X, X', X'' and X''' independently of one another are the same or different and stand for a cation of valency three, four, five and/or six, whereby the cations have ionic radii within the range 0.026–0.056 nm, Y*, Y', Y'' and Y''' independently of one another are the same or different and signify $(SO_4)^{2-}$ and/or $(PO_3F)^{2-}$, optionally together with $(CO_3)^{2-}$, whereby the proportion of $(CO_3)^{2-}$ is restricted to at most ⅙, relative to the molar quantities of Y, Y', Y'' and Y''', Q, Z, z', Z'', Z''', Z'''' and Z''''' independently of one another are the same or different and stand for $F^-$, $Cl^-$, $OH^-$ or $O^{-2}$, and C*, C' and C'' independently of one another are the same or different and are a monovalent cation, and also u, u' and u'' independently of one another are the same or different and are an integer or fraction within the range from 0 to 6 and specify the degree of substitution of B* by C*, of B'' by C' and of B''' by C''' in the respective cation sublattice, r is an integer or fraction within the range from 0 to 10 and specifies the degree of substitution of A' by B' in the cation sublattice, r' is an integer or fraction between 0 and 9 and specifies the degree of substitution of A'' by A''', s and s' independently of one another are the same or different and are an integer or fraction within the range from 0 to 6 and specify the degree of substitution of $X'O_4$ by Y' and of $X''O_4$ by $X'''O_4$ in the respective sublattice of the tetrahedral anions, and t and t' independently of one another are the same or different and are an integer or fraction within the range from 0 to 2 and specify, respectively, the degree of substitution of Z'' by Q and unoccupied lattice positions for type A3), in a dental material based on polymerisable, ethylenically unsaturated monomers by way of binding agent, a catalyst for cold polymerisation, hot polymerisation and/or photopolymerisation and, relative to the dental material, 1–95 wt-% of an inorganic filler in a quantity that is effective for the absorption of ions from the biological application environment.

The filling materials described in this application may, by reason of their outstanding optical properties, be employed in the visible region of the oral cavity and hence in direct contact with the saliva. The proportion of apatite in the filling can therefore give off ions (inter alia, fluoride, phosphate, calcium) to the saliva and to the surrounding dental enamel and also absorb them. The latter may also be effected from other external sources such as toothpaste.

The invention is elucidated further below on the basis of embodiment examples and comparative examples.

EXAMPLES

With a view to production of the pastes described below, use was made of a commercially available kneader manufactured by Grieser. Its kneading tools were modified in such a way that a particularly intensive intermixing and homogeneous distribution of the initial substances was possible. The homogenisation of the monomer mixtures was effected in conventional manner with the aid of a three-roll mill.

In the case of light-curing systems, the curing-time amounted to 40 sec with the aid of a commercially available lamp (Degulux® manufactured by Degussa).

Description of methods:
Refractive index:

The determination of the refractive index of the fine-grained pulverulent samples was effected by means of an embedding method under an optical microscope of the type JENAPOL INTERPHAKO (ZEISS). The powder sample is embedded in a liquid of known refractive index. At the phase boundary a bright line (BECKE line) is formed which, when the tube is raised, passes into the higher-refracting medium. The refractive index of the liquid phase is varied until agreement with the powder sample is obtained.

Transparency:

The determination of the transparency is effected on test samples having a thickness d=3.0±0.1 mm and a diameter of 20±0.1 mm. With a view to production of the samples, the composite paste that is poured into steel moulds of the same dimensions is loaded with 400 kp for 30 sec and then cured for 2 min with a dental lamp having a light intensity of at least 200 rel. units. During the curing process the surface of the composite is shielded from atmospheric oxygen by a transparent film. The measurement of the transparency is effected with a UV/VIS spectrophotometer PU8800 (Philips) in transmission mode.

Example 1

68.14 g silanised barium-silicate glass, 5 g aerosils and 4 g $Ca_{10}(PO_4)_6F_2$, $n_D$=1.63, with 0.034 wt-% camphor quinone are worked into 22.52 g of a monomer mixture consisting of 45 parts bis-GMA, 20 parts UDMA and 35 parts TRGDMA. The paste that forms is cured with light (Degulux®). A white, opaque paste is formed, which after curing exhibits a transparency of TR=18.6% (770 nm).

Example 2

68.14 g silanised barium-silicate glass, 5 g aerosils and 4 g $Ca_8Na_2[(PO_4)_4(SO_4)_2]F_2$, $n_D$=1.57, with 0.034 wt-% camphor quinone are worked into 22.52 g of a monomer mixture consisting of 45 parts bis-GMA, 20 parts UDMA and 35 parts TRGDMA. The paste that forms is cured with light (Degulux®). A white, transparent paste is formed, which after curing exhibits a transparency of TR=24.30% (770 nm). The increase in the transparency by 6% is sufficient in order to be able, by kneading in pigments, to dye the paste in a desired tooth colour without thereby losing the transparency which is similar to that of dental enamel, as in Example 1.

This behaviour applies to all the dental materials according to the invention.

What is claimed is:

1. Dental material based on polymerisable, ethylenically unsaturated monomers as binding agent, a polymerisation catalyst and, relative to the dental material, 1–95 wt-% of an inorganic filler having a refractive index <1.58, wherein the filler comprises:

A) at least one mixed apatite selected from the group consisting of

A1) $A_{10}(XO_4)_6Z_2/B^{-*}_{10-u}C^{-*}_u(Y^{-*})_6Z'_2$

A2) $A'_{10-r}(X'O_4)_{6-s}Z''_{2-t}/B'_r(Y')_sQ_t/B''_{10-u'}C'_{u'}(Y'')_6Z'''_2$ and A3) $A''_{10-r'}(X''O_4)_{6-s'}Z''''_{2-t'}/A'''_{r'}(X'''O_4)_{s'}/B'''_{10-u''}C''_{u''}(Y''')_6Z'''''_2$;

in which

A, A', A", A''', B-*, B', B" and B''' independently of one another are the same or different and stand for a bivalent cation or a charge-equivalent combination of monovalent and trivalent cations, whereby the cations have ionic radii within the range 0.069–0.174 nm, X, X', X" and X''' independently of one another are the same or different and stand for a cation of valency three, four, five or six, whereby the cations have ionic radii within the range 0.026–0.056 nm, Y-*, Y', Y" and Y''' independently of one another are the same or different and signify $(SO_4)^{2-}$ or $(PO_3F)^{2-}$, optionally together with $(CO_3)^{2-}$, whereby the proportion of $(CO_3)^{2-}$ is restricted to at most ⅙, relative to the molar quantities of Y-*, Y', Y" and Y''', Q, Z, Z', Z", Z''', Z'''' and Z''''' independently of one another are the same or different and stand for F⁻, Cl⁻, OH⁻ or $O^{2-}$, and C-*, C' and C" independently of one another are the same or different and are a monovalent cation, and also u, u' and u" independently of one another are the same or different and are an integer or fraction within the range from 0 to 6 and specify the degree of substitution of B-* by C-*, of B" by C' and of B''' by C" in the respective cation sublattice, r is an integer or fraction within the range from 0 to 10 and specifies the degree of substitution of A' by B' in the cation sublattice, r' is an integer or fraction between 0 and 9 and specifies the degree of substitution of A" by A''', s and s' independently of one another are the same or different and are an integer or fraction within the range from 0 to 6 and specify the degree of substitution of $X'O_4$ by Y' and of $X"O_4$ by $X'''O_4$ in the respective sublattice of the tetrahedral anions, and t and t' independently of one another are the same or different and are an integer or fraction within the range from 0 to 2 and specify, respectively, the degree of substitution of Z" by Q and unoccupied lattice positions for type A3), in a quantity that is effective for the absorption of ions from the biological application environment of the dental material.

2. Dental material according to claim 1, wherein the refractive index of filler component A) lies within the range from 1.50 to 1.66.

3. Dental material according to claim 1, wherein the particle size of filler component A) lies within the range from 0.01 to 10 μm.

4. Dental material according to claim 1, wherein A, A', A", A''', B-*, B', B" and B''' are the same or different and are each independently selected from the group consisting of $Mg^{2+}$, $Ca^{2+}$, $Sr^{2+}$, $Ba^{2+}$, $Y^{2+}$, $Ti^{2+}$, $Zr^{2+}$, $Mn^{2+}$, $Fe^{2+}$, $Pd^{2+}$, $Cu^{2+}$, $Ag^{2+}$, $Zn^{2+}$, $Sn^{2+}$, $RE^{2+}$, $RE^{3+}$, $Al^{3+}$, $In^{3+}$, $Y^{3+}$, $Na^+$ and $K^+$; wherein RE represents rare-earth metal.

5. Dental material according to claim 1, wherein X, X', X" and X''' are each the same or different and are each independently selected from the group consisting of $B^{3+}$, $Al^{3+}$, $Si^{4+}$, $P^{5+}$ and $S^{6+}$.

6. Dental material according to claim 1, wherein at least one of C*, C' and C" signify $Na^+$.

7. Dental material according to claim 1, wherein a proportion by weight of filler A) amounts to between 1 and 70 wt-%, relative to the dental material.

8. Dental material according to claim 1, wherein a proportion by weight of filler A) amounts to between 2 and 35 wt-%, relative to the dental material.

9. Dental material according to claim 1, wherein a proportion by weight of filler A) amounts to between 2 and 7 wt-%, relative to the dental material.

10. Dental material according to claim 1, comprising, in a mixture with component A), at least one member selected from the group consisting of B1) aspherical, fragmented powders comprising at least one member selected from the group consisting of quartz, glass ceramic and glass, having a refractive index from 1.46 to 1.58 and an average particle size from 0.5 to 5.0 µm;

B2) microscopic beads;

B3) inorganic fibres and

B4) organic fibres.

11. Dental material according to claim 10, wherein a weight ratio of A) to B) lies within the range from 10:1 to 1:30.

12. Dental material according to claim 1, further comprising filler C), in the finished, completely polymerised dental material, including globular particles based on $SiO_2$ comprising at least one member selected from the group consisting of C1) a spherical, polydisperse or monodisperse $SiO_2$ nucleus which is coated at individual points on its surface with metal-oxide particles, whereby the coated particles exhibit a refractive index from 1.45 to 1.62 and an average primary-particle size from 0.005 to 2 µm and the coating particles consisting of metal oxide have an average size of less than 60 nm, C2) $SiO_2$ having a refractive index between about 1.38 and <1.50 and an average primary-particle size from about 0.04 µm to 1.5 µm, C3) an $SiO_2$ nucleus which is coated with an oxide of at least one element of Groups I, II, III and IV of the Periodic Table, whereby the coated particles exhibit a refractive index from 1.45 to 1.62 and an average primary-particle size from 0.04 to 1.5 µm and the coating is between about 15 and 40 nm thick and C4) particles described under C1), C2) or C3) which in addition are covered with a layer comprising at least one member selected from the group consisting of a polymerisable organic binding agent based on (a) monofunctional or multifunctional (meth)acrylates and [/or] (b) reaction products of isocyanates and methacrylates that contain OH groups, whereby a primary-particle size of the particles that are provided with the layer of polymerisable binding agent is between about 0.04 and 1.5 µm, whereas thickness of the covering layer is in a range from 5 nm to 50 nm and refractive index of the coated particles lies within a range of 1.40–1.52.

13. Dental material according to claim 12, wherein a weight ratio of A) to C) lies within a range from 10:1 to 1:30.

14. Dental material according to claim 10, wherein a ratio of filler (B) to filler (C) is adjusted in such a way that an aggregation of the fillers (C) is avoided.

15. Dental material according to claim 10, wherein a ratio of (C) to (B) is adjusted within a range from 1:85 to 4:1 in such a way that strength of the dental material, in terms of its compressive strength, amounts to between >320 and 480 MPa.

16. Dental material according to claim 10, wherein a ratio of (C) to (B) amounts to $\geq 1:10$.

17. Dental material according to claim 10, wherein particles C) in finished, completely polymerised material are present separately as discrete particles.

18. A process for using at least one mixed apatite selected from the group consisting of:

A1) $A_{10}(XO_4)_6Z_2/B\text{-}^*{}_{10-u}C\text{-}^*{}_u(Y\text{-}^*)_6Z'_2$;

A2) $A'_{10-r}(X'O_4)_{6-s}Z''_{2-t}/B'_r(Y')_sQ_t/B''_{10-u'}C''_{u'}(Y'')_6Z'''_2$ and A3) $A''_{10-r}(X''O_4)_{6-s}Z'''_{2-t'}/A'''_{r'}(X'''O_4)_{s'}/B'''_{10-u''}C'_{u''}(Y''')_6Z''''_2$; in which A, A', A'', A''', B-*, B', B'' and B''' are independently of one another the same or different and stand for a bivalent cation or a charge-equivalent combination of monovalent and trivalent cations, whereby the cations have ionic radii within the range 0.069–0.174 nm, X, X', X'' and X''' independently of one another are the same or different and stand for a cation of valency three, four, five or six, whereby the cations have ionic radii within the range 0.026–0.056 nm, Y-*, Y', Y'' and Y''' independently of one another are the same or different and signify $(SO_4)^{2-}$ or $(PO_3F)^{2-}$, optionally together with $(CO_3)^{2-}$, whereby the proportion of $(CO_3)^{2-}$ is restricted to at most ⅙, relative to the molar quantities of Y, Y', Y'' and Y''', Q, Z, Z', Z'', Z''', Z'''' and Z''''' independently of one another are the same or different and stand for $F^-$, $Cl^-$, $OH^-$ or $O^{2-}$, and C-*, C' and C'' independently of one another are the same or different and are a monovalent cation, and also u, u' and u'' independently of one another are the same or different and are an integer or fraction within the range from 0 to 6 and specify the degree of substitution of B-* by C-*, of B'' by C' and of B''' by C''' in the respective cation sublattice, r is an integer or fraction within the range from 0 to 10 and specifies the degree of substitution of A' by B' in the cation sublattice, r' is an integer or fraction between 0 and 9 and specifies the degree of substitution of A'' by A''', s and s' independently of one another are the same or different and are an integer or fraction within the range from 0 to 6 and specify the degree of substitution of $X'O_4$ by Y' and of $X''O_4$ by $X'''O_4$ in the respective sublattice of the tetrahedral anions, and t and t' independently of one another are the same or different and are an integer or fraction within the range from 0 to 2 and specify, respectively, the degree of substitution of Z'' by Q and unoccupied lattice positions for type A3), in a dental material based on polymerisable, ethylenically unsaturated monomers as binding agent, a polymerisation catalyst and, relative to the dental material, 1–95 wt-% of an inorganic filler having a refractive index <1.58 in a quantity that is effective for the absorption of ions from the biological application environment.

* * * * *